(12) United States Patent
Kim et al.

(10) Patent No.: US 9,085,642 B2
(45) Date of Patent: Jul. 21, 2015

(54) PEPTIDE INHIBITING RANKL-RANK INTERACTION AND THE USE THEREOF

(71) Applicant: RESEARCH & BUSINESS FOUNDATION SUNGKYUNKWAN UNIVERSITY, Suwon-si (KR)

(72) Inventors: Kyeong Kyu Kim, Suwon-si (KR); Nacksung Kim, Gwangju-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 0 days.

(21) Appl. No.: 13/927,360

(22) Filed: Jun. 26, 2013

(65) Prior Publication Data

US 2014/0371143 A1 Dec. 18, 2014

(30) Foreign Application Priority Data

Jun. 18, 2013 (KR) ........................ 10-2013-0069759

(51) Int. Cl.
| | |
|---|---|
| *A61K 38/00* | (2006.01) |
| *A61K 38/04* | (2006.01) |
| *A61K 38/08* | (2006.01) |
| *C07K 4/00* | (2006.01) |
| *C07K 7/04* | (2006.01) |
| *C07K 7/06* | (2006.01) |
| *C07K 14/705* | (2006.01) |
| *C07K 7/00* | (2006.01) |
| *C07K 7/64* | (2006.01) |

(52) U.S. Cl.
CPC .............. *C07K 14/70578* (2013.01); *C07K 7/00* (2013.01); *C07K 7/64* (2013.01)

(58) Field of Classification Search
None
See application file for complete search history.

(56) References Cited

FOREIGN PATENT DOCUMENTS

| KR | 10-0690230 | 3/2007 |
| KR | 10-1180431 | 9/2012 |
| WO | WO 2011/149310 A2 * | 1/2011 |

OTHER PUBLICATIONS

Wells, 1990, Biochemistry 29:8509-8517.*
Ngo et al., 1994, The Protein Folding Problem and Tertiary Structure Prediction, Merz et al., eds., Birkhauser, Boston, pp. 492-495.*
Tokuriki et al., 2009, Curr. Opin. Struc. Biol. 19:596-604.*
Simonet, W. S., et al. "Osteoprotegerin: a novel secreted protein involved in the regulation of bone density." Cell 89.2 (1997): 309-319.
Yasuda, Hisataka, et al. "Osteoclast differentiation factor is a ligand for steoprotegerin/osteoclastogenesis-inhibitory factor and is identical to TRANCE/RANKL." Proceedings of the National Academy of Sciences 95.7 (1998): 3597-3602.
Yasuda, Hisataka, et al. "Identity of osteoclastogenesis inhibitory factor (OCIF) and osteoprotegerin (OPG): a mechanism by which OPG/OCIF inhibits osteoclastogenesis in vitro." Endocrinology 139.3 (1998): 1329-1337.
Fata, Jimmie E., et al. "The osteoclast differentiation factor osteoprotegerin-ligand is essential for mammary gland development." Cell 103.1 (2000): 41-50.
Vega, Damaris, Naim M. Maalouf, and Khashayar Sakhaee. "The role of receptor activator of nuclear factor-$_K$ B (RANK)/RANK ligand/osteoprotegerin: clinical implications." Journal of Clinical Endocrinology & Metabolism 92.12 (2007): 4514-4521.
Excerpt: Hai, Ta Minh. "The structural and functional studies of mouse RANKL-RANK complex and bacterial aminopeptidase PepS". Thesis for the Degree of Doctor of Philosophy. Feb. 2010 (9 pages, in English).

* cited by examiner

*Primary Examiner* — Elizabeth C Kemmerer
(74) *Attorney, Agent, or Firm* — NSIP Law (57) ABSTRACT

Provided are a peptide for inhibiting an interaction between an RANKL and an RANK consisting of an amino acid sequence of SEQ ID NO: 1 and a pharmaceutical composition for preventing or treating bone diseases including the peptide. The peptide consisting of an amino acid sequence of SEQ ID NO: 1 is not present in a cyclic shape, and has 10 or less amino acids, thereby having better biostability than a conventional peptide to inhibit an RANKL-RANK interaction, being preferable in price during synthesis, and having a better RANKL-RANK interaction inhibitory effect. For this reason, the peptide may be used as an effective component of the composition effectively inhibiting differentiation of osteoclasts. A pharmaceutical composition including the peptide is bound with the RANKL and the peptide, instead of the RANK, thereby inhibiting the interaction between the RANKL and the RANK, and thus inhibiting osteoclast differentiation.

9 Claims, 7 Drawing Sheets

PEPTIDE INHIBITING RANKL-RANK INTERACTION AND THE USE THEREOF

CROSS-REFERENCE TO RELATED APPLICATION

This application claims priority to and the benefit of Korean Patent Application No. 10-2013-0069759, filed Jun. 18, 2013, the disclosure of which is incorporated herein by reference in its entirety.

BACKGROUND

1. Field of the Invention

The present invention relates to a new peptide inhibiting an interaction between a receptor activator of a nuclear factor K-B ligand (RANKL) and a receptor activator of a nuclear factor K-B (RANK) and a use thereof.

2. Discussion of Related Art

A bone is an important part of a human body supporting soft tissues and a body weight thereof, surrounding internal organs to protect them from external impact and structurally support muscles or organs, and storing calcium or other essential inorganic substances in the body, and a special organ maintained by a balance between bone resorption by osteoclasts and bone formation by osteoblasts. An RANKL-RANK-osteoprotegerin (OPG) system has led to revolutionary advances in bone biology. An interaction between an osteoblast, an RANKL of a matrix cell, and an RANK receptor of an osteoclast leads to maturation of the osteoclast and thereby bone resorption (Yasuda, H., et al. 1998. Osteoclast differentiation factor is a ligand for an osteoprotegerin/osteoclastogenesis-inhibitory factor and is identical to TRANCE/RANKL. Proc. Natl. Acad. Sci. U.S.A. 95:3597-602). An OPG serves as a water-soluble induced receptor with respect to an RANKL and competes with an RANK to be bound with the RANKL. That is, when the RANKL binds to the RANK, which is a receptor present on a surface of an osteoclast precursor cell, the osteoclast precursor cell is matured into an osteoclast, thereby inducing bone resorption, and when the OPG is bound with the RANKL, the bonding between the RANKL and the RANK is interrupted, thereby inhibiting the osteoclastogenesis and preventing unnecessary bone resorption. Accordingly, the OPG has been known as an effective inhibitor against maturation and activation of osteoclasts in vivo or in vitro (Simonet, W. S., et al. 1997. Osteoprotegerin: a novel secreted protein involved in the regulation of bone density. Cell. 89:309-19; Yasuda, H., et al. 1998. Identity of osteoclastogenesis inhibitory factor (OCIF) and osteoprotegerin (OPG): a mechanism by which OPG/OCIF inhibits osteoclastogenesis in vitro. Endocrinology. 139:1329-337). Moreover, osteoblast/matrix cells (stromal cells), osteoclast precursors, and RANKL/RANK/OPG may be expressed into various skin cells, and thus functions thereof are involved in various different biological functions. The bonding of the RANKL/RANK has been known to regulate formation of lymph nodes and mammary glands during pregnancy and a body temperature of a female (Fata, J. E., et al. 2000. The osteoclast differentiation factor osteoprotegerin-ligand is essential for mammary gland development. Cell 103:41-50).

A ratio between the RANKL and the OPG regulates bone metabolism by bone genesis or bone resorption. Accordingly, if the ratio is not appropriately regulated, there is an imbalance between the bone genesis and the bone resorption, and bone diseases such as osteoporosis, rheumatoid arthritis, bone disruption, etc. are induced (Vega, D., Maalouf, N. M., and Sakhaee, K. 2007. CLINICAL Review #: the role of receptor activator of nuclear factor-kappaB (RANK)/RANK ligand/osteoprotegerin: clinical implications. J. Clin. Endocrinol. Metab. 92(12):4514-21.). Mutation of RANKs, OPGs and RANKLs known to humans is involved in unusual genetic skeletal dysplasia such as autosomal recessive osteopetrosis (ARO), expansile skeletal hyperphosphatasia (ESH), familial expansile osteolysis (FEO), early-onset Paget's disease, and Juvenile Paget's disease (JPD). In the bone metabolism, roles of RANKL/RANK/OPG proteins are important, and thus the bondings between them are considered an important goal to inhibit bone metabolism-related diseases.

To this end, today, various therapeutic methods such as OPG-Fc, RANK-Fc, an anti-RANKL antibody, and an RANKL vaccine are being developed, and peptides (OP3-4, WP9QY) modeled on an RANKL-binding loop of an OPG or TNF receptor having an effect of interrupting RANKL signal transduction are developed.

Meanwhile, the RANKL-RANK is included in the family of tumor necrosis factor (TNF) ligands-receptors, which have similar bonding types. That is, according to the bonding type, bonding receptors bind to grooves at a binding part of monomers of a ligand of a trimer formed by edge-to-face packing of subunits of a monomer. The inventors developed a peptide inhibiting the RANKL-RANK interaction in the prior art (referred to Korean Patent No. 10-1180431). The peptide had 10 or more amino acids and was designed in a cyclic shape by tagging cysteine (Cys) at the end of the peptide to make it similar to an RANK peptide. However, the peptide in the prior art was decreased in biostability, and disadvantageous in price during synthesis.

SUMMARY OF THE INVENTION

The present invention is directed to providing a peptide for inhibiting an interaction between an RANKL and an RANK, which is not formed in a cyclic shape, has an amino acid sequence of SEQ ID NO: 1 including 10 or less amino acids, and has excellent biostability and an excellent RANKL-RANK interaction inhibitory effect.

The present invention is also directed to providing a pharmaceutical composition for preventing or treating bond diseases including the peptide and a pharmaceutically available carrier.

Moreover, the present invention is also directed to providing a polynucleotide encoding the peptide.

Furthermore, the present invention is also directed to providing a recombinant vector including the polynucleotide.

However, the technical object of the present invention is not limited to the above-described objects, and other objects that are not described will be clearly understood by those of ordinary skill in the art from the following description.

One aspect of the present invention provides a peptide for inhibiting an interaction between an RANKL and an RANK, which has an amino acid sequence of SEQ ID NO: 1.

In one exemplary embodiment of the present invention, the peptide has a disulfide bond by linking $3^{rd}$ and $5^{th}$ amino acids.

In another exemplary embodiment of the present invention, the peptide inhibits the interaction between the RANKL and the RANK, and thus inhibits osteoclast differentiation.

Another aspect of the present invention provides a pharmaceutical composition for preventing or treating bone diseases, which includes the peptide and a pharmaceutically available carrier.

In one exemplary embodiment of the present invention, the bone disease is a disease induced by differentiation and activation of osteoclasts.

In another exemplary embodiment of the present invention, the bone disease is selected from the group consisting of osteoporosis, osteogenesis imperfecta, hypercalcemia, osteomalacia, rheumatoid arthritis, Paget's disease, bone loss by cancer, and osteonecrosis.

Furthermore, still another aspect of the present invention provides a polynucleotide encoding the peptide.

In addition, yet another aspect of the present invention provides a recombinant vector including the polynucleotide.

BRIEF DESCRIPTION OF THE DRAWINGS

The above and other objects, features, and advantages of the present invention will become more apparent to those of ordinary skill in the art by describing in detail exemplary embodiments thereof with reference to the adhered drawings, in which.

DETAILED DESCRIPTION OF EXEMPLARY EMBODIMENTS

Hereinafter, exemplary embodiments of the present invention will be described in detail. However, the present invention is not limited to the embodiments disclosed below, but can be implemented in various forms. The following embodiments are described in order to enable those of ordinary skill in the related art to embody and practice the present invention.

Although the terms first, second, etc. may be used to describe various elements, these elements are not limited by these terms. These terms are only used to distinguish one element from another. For example, a first element could be termed a second element, and, similarly, a second element could be termed a first element, without departing from the scope of exemplary embodiments. The term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

The terminology used herein is for the purpose of describing particular embodiments only and is not intended to be limiting of exemplary embodiments. The singular forms "a," "an," and "the" are intended to include the plural forms as well, unless the context clearly indicates otherwise. It will be further understood that the terms "comprises," "comprising," "includes," and/or "including," when used herein, specify the presence of stated features, integers, steps, operations, elements, components, and/or groups thereof, but do not preclude the presence or addition of one or more other features, integers, steps, operations, elements, components, and/or groups thereof.

With reference to the appended drawings, exemplary embodiments of the present invention will be described in detail below. To aid in understanding the present invention, like numbers refer to like elements throughout the description of the figures, and the description of the same elements will be not reiterated.

The inventors completed the present invention by identifying a crystal structure of a rat RANKL-RANK complex having a size of a 2.5 Å and a specific structure involved in the structure and bonding of the RANKL-RANK complex, and developing a novel peptide (L3-3B) formed in a non-cyclic shape and effectively inhibiting an RANKL-RANK interaction as a result of research to find a structural crystal factor determining specific recognition between a ligand and a receptor and provide a molecular level basis for continuous research on bone-related diseases and development of a new drug.

Hereinafter, the present invention will be described in detail.

The present invention provides a peptide for inhibiting an interaction between an RANKL and an RANK, which has an amino acid sequence of SEQ ID NO: 1. Particularly, the peptide according to the present invention has 8 amino acids of "Ser-Asp-Cys-Glu-Cys-Ser-Arg-Arg," in which cysteines located at $3^{rd}$ and $5^{th}$ amino acid positions are linked to each other, thereby forming a disulfide bond. Here, the "disulfide bond" refers to a covalent bond formed by oxidizing (dehydrogenizing) two sulfur atoms.

When the peptide according to the present invention is added, the RANKL is bound to the peptide according to the present invention, instead of the RANK, thereby inhibiting the interaction between the RANKL and the RANK and thus inhibiting the differentiation of osteoclasts. As a result, bone diseases by the differentiation or activation of the osteoclasts may be prevented or treated.

According to one exemplary embodiment of the present invention, as a result of the analysis of osteoclast differentiation to measure an inhibitory activity of a peptide regarding differentiation of osteoclasts by a bonding between the RANKL and the RANK, it was confirmed that the peptide according to the present invention exhibits an excellent inhibitory effect on osteoclast differentiation, compared with a control (referred to Example 6).

To this end, the present invention provides a pharmaceutical composition for preventing or treating bone diseases, which includes the peptide and a pharmaceutically available carrier.

The term "prevention" used herein refers to all actions inhibiting bone diseases or delaying occurrence of diseases by administering the composition of the present invention.

The term "treatment" used herein refers to all actions improving symptoms of a bone disease or altering for the better by administering the composition of the present invention.

In the present invention, the bone disease is a disease induced by differentiation and activation of osteoclasts, and particularly, selected from the group consisting of osteoporosis, osteogenesis imperfecta, hypercalcemia, osteomalacia, rheumatoid arthritis, Paget's disease, bone loss by cancer, and osteonecrosis, but the present invention is not limited thereto.

In the present invention, the pharmaceutically available carrier may be, but is not limited to, saline, buffer saline, water, glycerol, polyethylene glycol, vegetable oil, isopropyl myristate, or ethanol, but the present invention is not limited thereto.

When the pharmaceutical composition according to the present invention is formulated, a filler, an extender, a binder, a wetting agent, a disintegrating agent, a diluting agent such as a surfactant, or an excipient is generally used.

In solid preparations for oral administration, a tablet, a pill, powder, a granule, a capsule, a troche, etc. are included, and such a solid preparation is prepared by mixing at least one excipient such as starch, calcium carbonate, sucrose or lactose, or gelatin with the peptide according to the present invention, and in addition to the simple excipient, lubricants such as magnesium stearate talc are used. As liquid formulations for oral administration, a suspension, a solution for external/internal use, an emulsion, and a syrup are included, and in such a liquid formulation, various excipients, for example, a wetting agent, a sweetening agent, a flavoring agent, a preservative, etc. may be included, in addition to a simple diluting agent such as water or liquid paraffin.

Preparations for non-oral administration include a distilled aqueous solution, a non-aqueous solvent, a suspension solvent, an emulsion, a lyophilized preparation, and a suppository.

As a non-aqueous solvent or suspension solvent, vegetable oil such as propylene glycol, polyethylene glycol, or olive oil or an injectable ester such as ethylolate may be used. As a base of the suppository, witepsol, macrogol, tween 61, cacao butter, laurinum, glycerol, or gelatin may be used.

The composition according to the present invention may be administered in an oral or parenteral route (e.g., intravenous, subcutaneous, abdominal, or local administration) depending on a desired method, and an administration amount may be suitably selected by one of ordinary skill in the art according to a patient's condition and body weight, severity of illness, a drug form, a route of administration, and duration of administration.

The composition according to the present invention is administered in a pharmaceutically effective amount. The term "pharmaceutically effective amount" means an amount sufficient to treat a disease with a reasonable benefit/risk ratio applicable to the medical treatment, and the effective dose level may be determined by the kind of a patient's disease, severity, activity of a drug, sensitivity to a drug, duration of administration, a route of administration, an excretion ratio, duration of treatment, a factor including concurrently-used medications, and other factors well known in a medical field.

The composition according to the present invention may be administered individually as a medicine or in combination with a different medicine, sequentially or simultaneously administered with a conventional medicine, and administered once or multiple times. In consideration of all of the above-described factors, it is important to administer the composition at an amount capable of obtaining the maximum effect with the minimum amount without side effects, and the amount may be easily determined by one of ordinary skill in the art.

Specifically, an effective amount of the composition according to the present invention may be dependent on an age, gender, or body weight of a patient, and generally, the composition may be administered at 0.001 to 150 mg, and preferably, 0.01 to 100 mg, per 1 kg of a body weight, daily or every other day, or once to three times per day. However, since the effective amount of the composition may vary according to a route of administration, severity of obesity, gender, body weight, or age, and therefore, the scope of the present invention is not limited to the effective amount of the composition by any method.

Meanwhile, the peptide according to the present invention may be prepared by a general chemical synthesis, for example, solid-phase peptide synthesis, but the present invention is not limited thereto, or by culturing a microorganism which is transformed by a recombinant vector containing a polynucleotide encoding the peptide to express the peptide, and purifying the peptide by a common method.

To this end, the present invention provides a polynucleotide encoding the peptide.

In addition, the present invention provides a recombinant vector including the polynucleotide.

The term "vector" used herein refers to any DNA construct containing a DNA sequence operably linked to a suitable regulation sequence capable of expressing DNA in a suitable host. The vector may be a plasmid, a phage particle, or a simple latent genome insert. When the vector is transformed into an appropriate host, the vector may be capable of being replicated or functioned irrespective of a host genome, or integrated into the genome itself in some cases. Since a plasmid is currently the most conventionally-used type of vectors, the terms "plasmid" and "vector" used herein are used interchangeably sometimes because a plasmid is currently the most prevailing type of the vectors, and according to the present invention, the plasmid is preferably a plasmid vector. A conventional plasmid vector capable of being used for such a purpose may have a structure including (a) a replication origin making efficient replication such that several hundreds of plasmid vectors are included in one host cell, (b) an antibiotic resistance gene used to select host cells transformed by the plasmid vectors, and (c) a restriction site into which a foreign DNA fragment may be inserted. Though there is no suitable restriction site, the vector may be easily ligated with the foreign DNA using a synthetic oligonucleotide adaptor or a linker according to a conventional method.

In the present invention, the "transformation" refers to a phenomenon of introducing external DNA into a host cell to serve as a chromosomal factor or be replicable by chromosomal integration, resulting in artificially inducing a genetic engineering change. Generally, in the transformation methods, electroporation, $CaPO_4$ precipitation, $CaCl_2$ precipitation, microinjection, and lithium acetate-DMSO method are included. To manufacture transformed recombinant microorganisms, a host cell having a high DNA induction efficiency and high efficiency of expressing the introduced DNA is generally used, and the host cells may be all microorganisms including prokaryotic and eukaryotic cells, for example, bacteria, yeasts, and fungi.

Hereinafter, to help understanding of the present invention, exemplary Examples will be provided. However, the following Examples are merely provided to make the present invention more easily understood, not to limit the present invention.

EXAMPLES

In Examples of the present invention, to confirm a structure of an RANKL-RANK complex, rat RANK and RANKL ectodomains were used, the "eRANK and eRANKL" refer to the RANK ectodomain and RANKL ectodomain, respectively, and for convenience, the eRANK and eRANKL were expressed as the RANK and the RANKL.

Example 1

Analysis of Structure of RANKL-RANK Complex

To manufacture a peptide inhibiting an interaction between an RANKL and an RANK, a structure of the RANKL-RANK complex was determined as follows.

Figure 1:
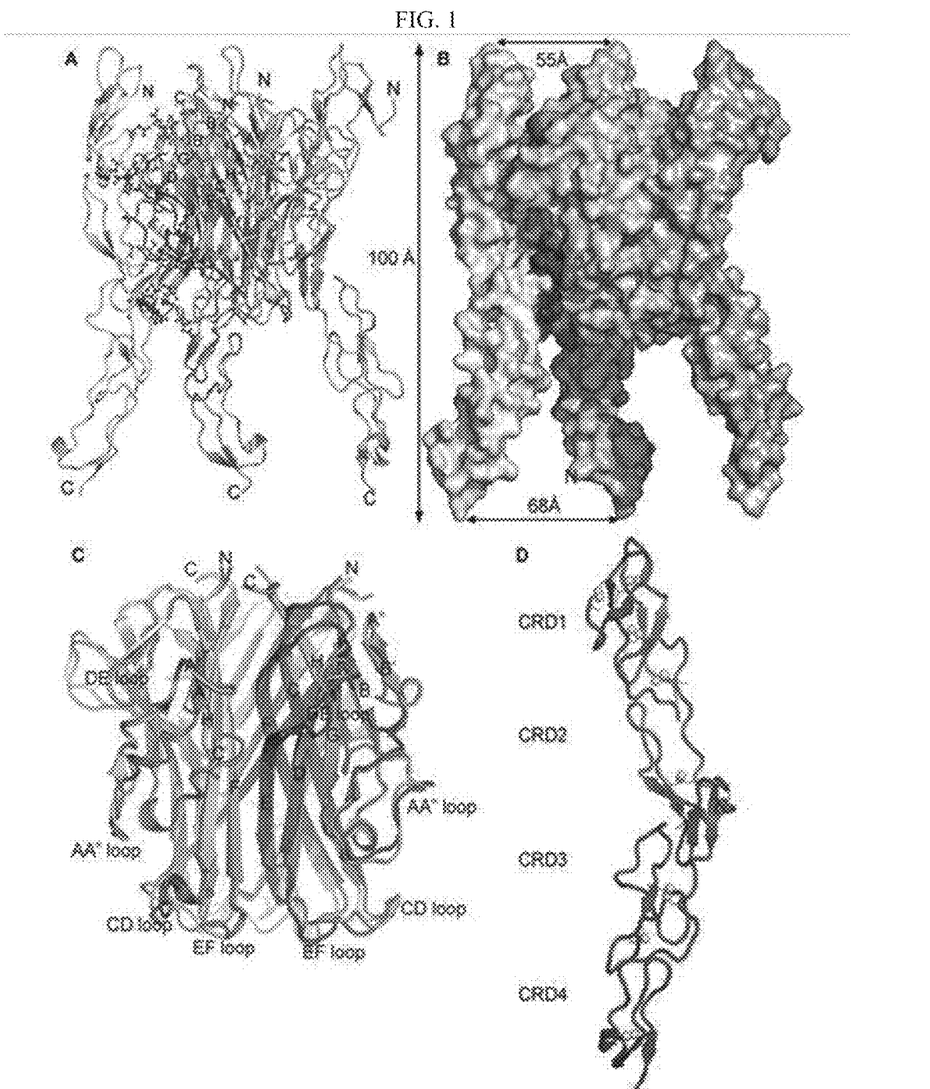
FIG. 1 shows diagrams of overall structures of an eRANK, an eRANKL, and an eRANK-eRANKL complex (A:tertiary structure of eRANK-eRANKL complex, B:binding surface of eRANK-eRANKL complex, C:overalp of free eRANKL and eRANK-binding RANKL, loop 1 (red), loop 2 (green), loop 3 (blue), and D: structure of RANK)
Figure 2:
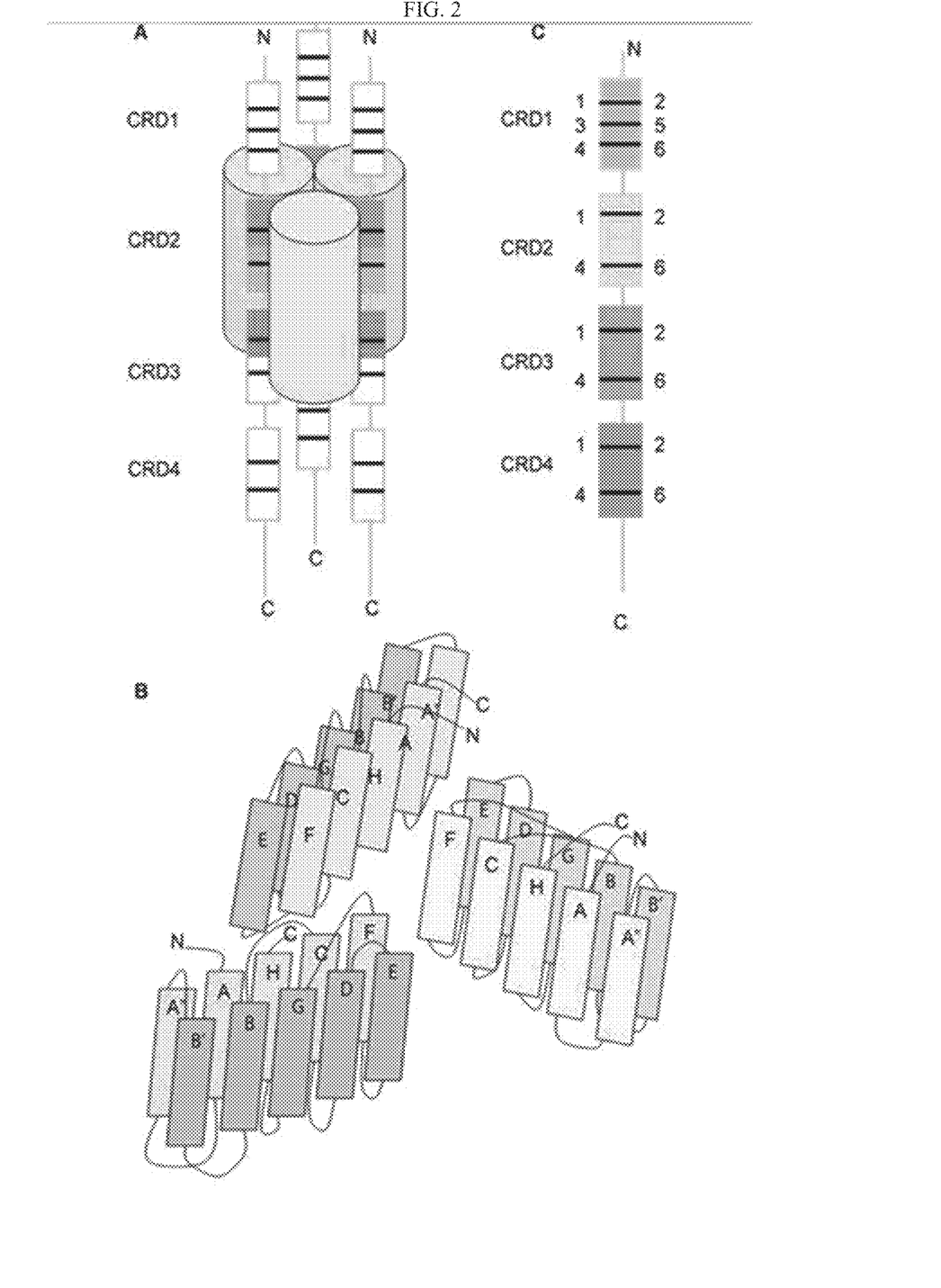
FIG. 2 shows diagrams of an eRANK, an eRANKL, and an eRANK-eRANKL complex (A: eRANK-eRANKL complex, B: eRANKL trimer, and C: eRANK)

That is, the structure of the RANKL-RANK complex was determined by a molecular replacement method using a crystal structure of the RANKL as a search probe. The final model of the complex was composed of RANKL residue 161-315 and RANK residue 35-198. It was confirmed that the complex formed in a size of approximately 60 Å×70 Å×100 Å was composed of three RANK molecules including four cysteine-rich domains (CRDs), which were inserted into three gaps formed in a boundary surface of a subunit of a trimer RANKL (referred to FIGS. 1A, 1B, and 2). Like other TNF-series ligands, a RANKL monomer is composed of one jellyroll β-sandwich and two antiparallel β-pleated sheets, and RANKL trimer self-assembly was induced by a conserved hydrophobic interaction mostly formed by aromatic residues and hydrogen bonds of specific inter-subunits (referred to FIGS. 1D, 2A, and 2B). It was confirmed that when the RANK bound to the RANKL, structures of AA', CD, and EF loops were changed, and thus N- and C-terminals of strand D and E were transformed (referred to FIG. 1C).

Example 2

Analysis of RANK Structure

In Example 2, a specific RANK structure involved in the interaction between the RANKL and the RANK was confirmed.

It was confirmed that the RANK included four CRDs (referred to FIG. 1C), and had different structural characteristics from other general TNF-series receptors. It was confirmed that, in each CRD of the general TNF-series receptor, 6 conserved Cys residues formed a pair of disulfide bonds, whereas, in CRD2-CRD4 of the RANK, there were no $3^{rd}$ and $4^{th}$ Cys residues (referred to FIG. 1C). It was also confirmed that there was an unusual disulfide bond, for example, Cys125-Cys127, in the CRD3 (referred to FIG. 1D), and such a specific disulfide bond can be expected to be involved in RANKL-RANK recognition specificity.

Example 3

Confirmation of Main Bondings on RANKL-RANK Binding Surface

Figure 3:
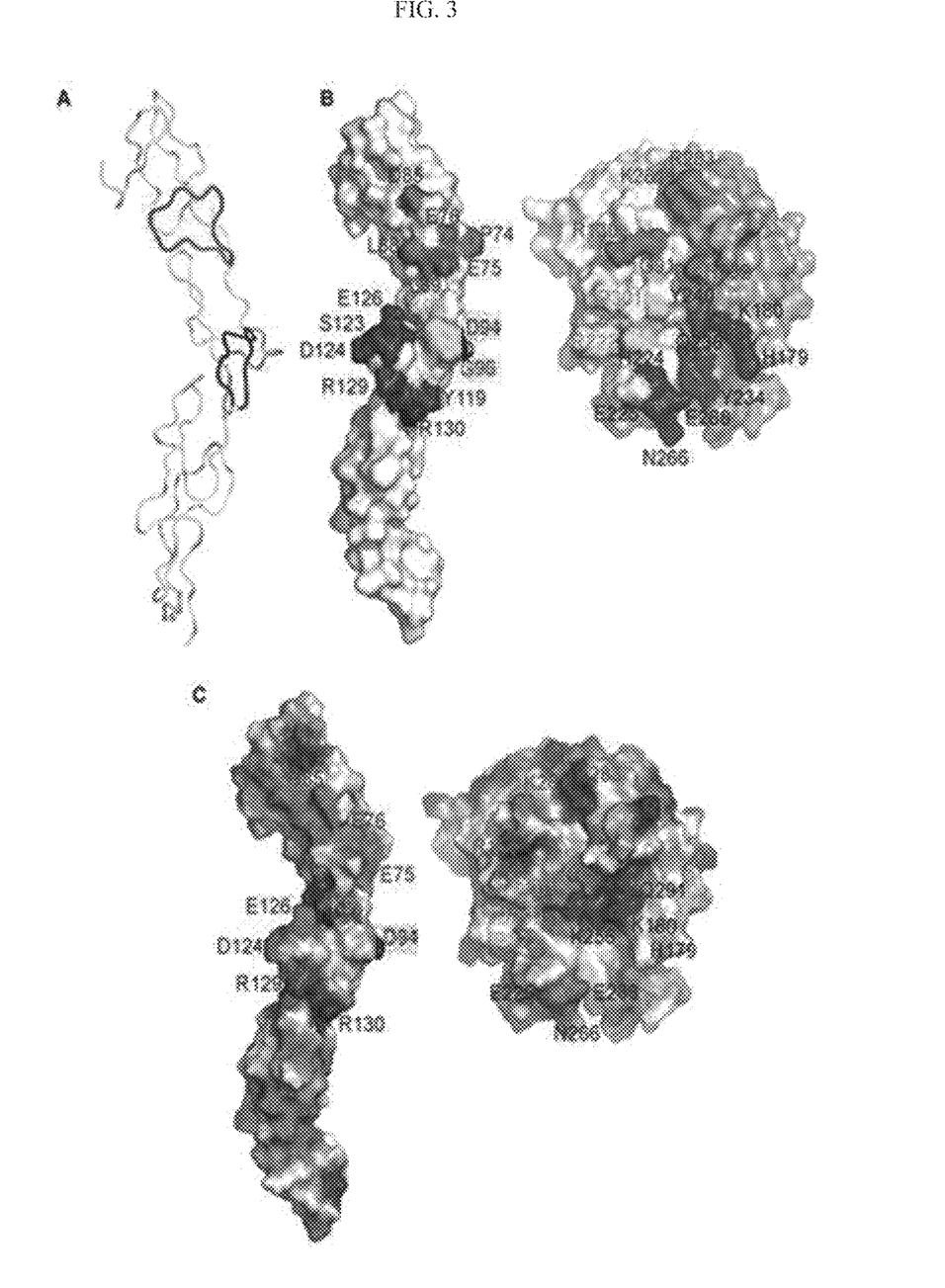
FIG. 3 shows diagrams of specific recognition sites of a ligand-receptor (A: loop 1 (red), loop 2 (green), and loop 3 (blue) of RANKL, B: RANKL and RANK-binding surface, and C: electrostatic mark on RANKL and RANK-binding surface)

In Example 3, bondings present on an RANKL-RANK binding surface were examined. That is, it was confirmed that, in the RANKL-RANK complex, two loops (loop 1 and loop 2) of CDR2 and one loop (loop 3) of CDR3 interacted with the RANKL (referred to FIG. 3). The binding of RANK to the RANKL reduced a solvent accessible surface area by 7680 $Å^2$, which corresponded to 15.4% of a total accessible surface area to a solution of unbinding receptors and ligands. It was confirmed that charged residues of the receptors and ligands provided an electrostatic network determining recognition specificity between the receptor and the ligand (referred to FIG. 3C).

Figure 4:
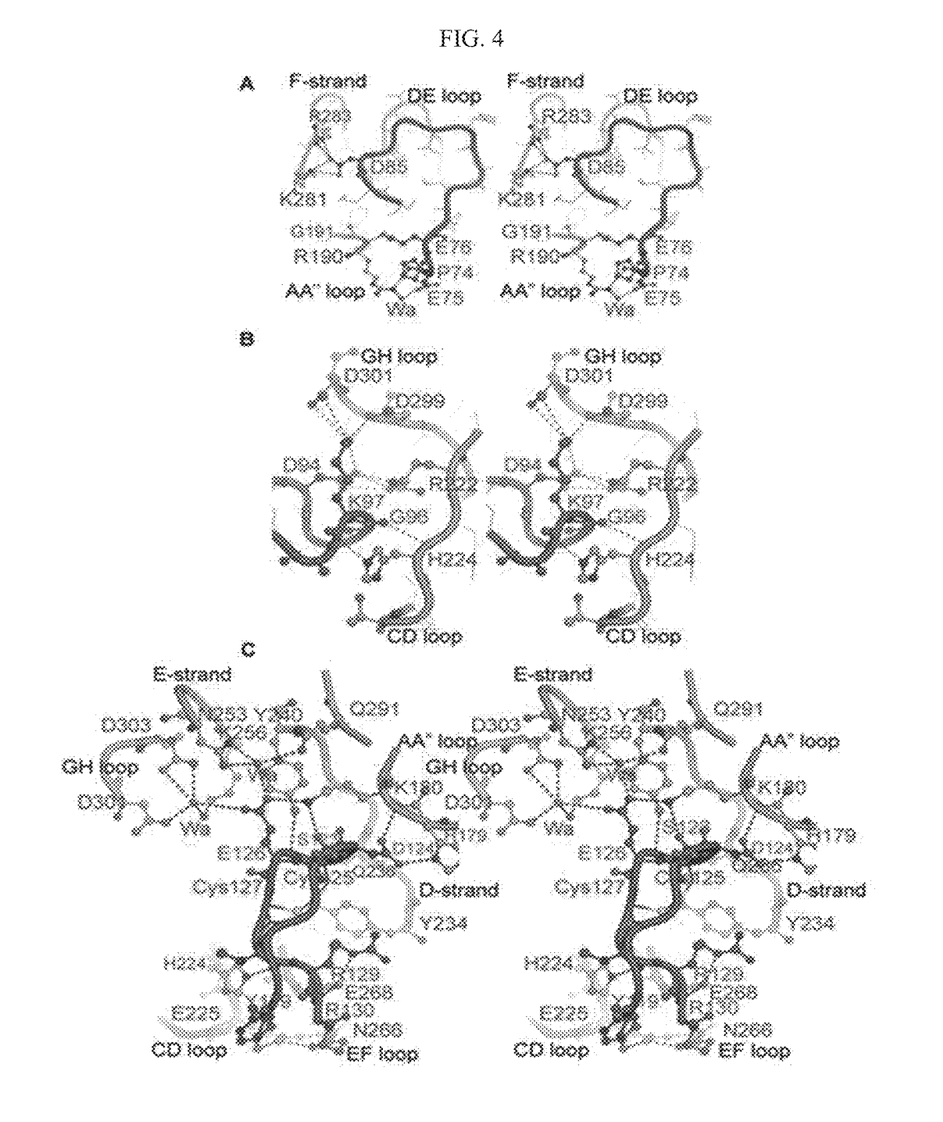
FIG. 4 shows diagrams of an interaction between residues present on a binding surface of the eRANK-eRANKL complex (A:loop 1, B:loop 2, C:loop 3, the green part represents an RANKL, and the red part represents an RANK)

In loop 1, Asp85 of the RANK interacted with Lys281 and Arg283 of strand F of the RANKL by ionic bonds and hydrogen bonds, and in loop AA' of the RANKL, Arg190 and Gly191 formed hydrogen bonds respectively with a carbonyl group of a backbone of Pro74 and a side chain of Glu76, thereby further stabilizing the RANKL-RANK complex (referred to FIG. 4A and Table 1). Further, Asp75 of the RANK formed ionic bonds and a water-mediated hydrogen bond with Arg190 of the RANKL, and van der Waals bonds present in Leu88(eRANK)-His252(eRANKL) and Leu89(eRANK)-Gln302(eRANKL) made the recognition specificity of the complex further increased (referred to FIG. 4A and Table 1).

Three residues (Asp94, Gly96, and Lys97) of loop 2 were in contact with the RANKL in a wide range, and such wide interactions were formed between Asp94 and Lys97 of the RANK, and Arg222, Asp299, and Asp301 of the RANKL. Here, Asp94 formed a charge-enhanced hydrogen bond with Arg222, and Lys97 interacted with two acidic residues such as Asp299 and Asp301. At the same time, Asp94 and Lys97 were involved in intra-subunit salt bridges, which was important to determine an overall shape of loop 2. Moreover, additional hydrogen bonds were present between backbone carbonyl oxygens of Gly96 and Lys97 and the backbone and side chain nitrogen of His224 (referred to FIG. 4B and Table 1).

Loop 3 provided the largest binding surface. Backbone carbonyl atoms of Tyr119 and Ser123 formed hydrogen bonds respectively with Glu225 and Lys180 of the RANKL (referred to FIG. 4C and Table 1), a side chain and a backbone carbonyl oxygen of RANK Asp124 formed hydrogen bonds respectively with His179 and a salt bridge, Lys180. Backbone carbonyl groups of Cys125 and Cys128 formed hydrogen bonds respectively with Gln236/Tyr240 and His224 of the RANKL. A wide-range of hydrogen bonds and salt bridges were observed between Arg129 and Arg130 of the RANK, and Glu225, Glu268, and Asn266 of the RANKL (referred to FIG. 4C and Table 1).

Figure 5:
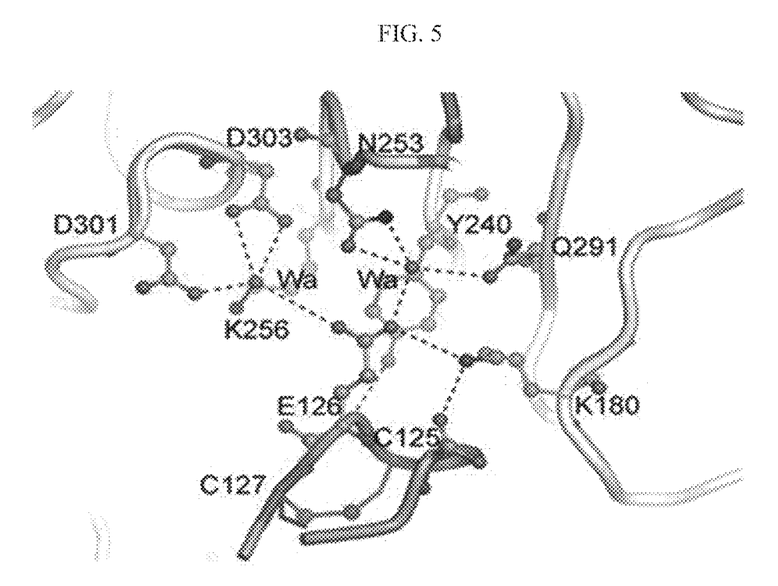
FIG. 5 is a diagram of a ball-and-stick model of functional residues of loop3.

The most outstanding characteristic of loop 3 is the presence of a specific disulfide bond at the end of the loop formed between Cys125 and Cys127. The specific disulfide bond is an important factor to determine a shape of loop 3 and make Glu126 widely interacting with various residues of the RANKL. Glu126 interacted with Lys180 of the RANKL (referred to FIG. 5), and also formed bidentate water-mediated hydrogen bonds with Lys256, Asp301, and Asp303 on one side, and Asn253 and Gln291 on the other side. In addition, it was confirmed that Glu126 formed a van der Waals bond with Tyr240 (referred to FIG. 5).

As a result of examining the method of binding loops 1, 2, and 3 with the RANKL, loop 2 was widely bound with the RANKL via Asp94, Gly96, and Lys97 though it had a relatively smaller size, and loop 3 provided the widest binding surface and formed the most bonds with the RANKL. Accordingly, the inventors manufactured some peptides expected to be bound with the RANKL from an amino acid sequence of loop 3 based on the above-described structural data.

TABLE 1

Main residues involved in RANKL-RANK interaction

| | RANK | RANKL | Kind of bonding |
|---|---|---|---|
| Loop 1 | Pro74 | Arg190 | hydrogen bond |
| | Asp75 | Arg190 | ionic, hydrogen bond |
| | Glu76 | Gly191 | hydrogen bond |
| | Asp85 | Lys281, Arg283 | ionic, hydrogen bond |
| | Leu88 | His252 | hydrophobic |
| | Leu89 | Gln302 | hydrophobic |
| Loop 2 | Asp94 | Arg222 | ionic, hydrogen bond |
| | Gly96 | His224 | hydrogen bond |
| | Lys97 | Asp301, Asp299 | ionic, hydrogen bond |
| Loop 3 | Tyr119 | Glu225 | hydrogen bond |
| | Ser123 | Lys180 | hydrogen bond |
| | Asp124 | His179, Lys180 | ionic, hydrogen bond |
| | Cys125 | Tyr240, Gln236 | hydrogen bond |
| | Glu126 | Lys180 | ionic, hydrogen bond |
| | Glu126 | Tyr240 | hydrophobic |
| | Cys128 | His224 | hydrogen bond |
| | Arg129 | Tyr234 | hydrophobic |
| | Arg129 | Glu268 | ionic, hydrogen bond |
| | Arg130 | Glu225, Asn266 | ionic, hydrogen bond |

Example 4

Cloning of Genes Encoding eRANKL and eRANK, and Expression and Purification of eRANKL and eRANK Proteins To obtain the RANKL-RANK complex, ectodomains of the RANKL (eRANKL, residues 157-316) and the RANK (eRANK, residue 32-201) of rates were expressed and purified by the same methods as each other. Genes encoding the eRANKL and eRANK were cloned using a pVFT3S vector having a restriction site of a tobacco etch virus (TEV) protease between N-terminal 6His-thioredoxin (Trx) and inserted cDNA (referred to Korean Patent No. 10-0690230). The manufactured 6His-Trx-eRANKL and 6His-Trx-eR-ANK were induced with 0.2 mM isopropyl-β-D-thiogalactoside (IPTG) at 15° C. for 24 hours, and expressed in *Escherichia coli* BL21 (DE3) and Origami cells (Novagen, Wis., USA), respectively. Each fusion protein was purified by a metal affinity purification method using a Ni-NTA column (GE Healthcare, Uppsala, Sweden), and lysed by the TEV protease. The lysed RANKL and RANK were put again into an NTA column, and a part passing through the column was injected through a Superdex-200 gel filtration chromatography (GE Healthcare, Uppsala, Sweden) having an equilibrium with a buffer (25 mM Tris-HCl (pH 7.5), 50 mM NaCl) to purify.

Example 5

Manufacture of Polypeptides L3-3, L3-3S, L3-3N, L3-3A, and L3-3B

To provide a medicine for bone diseases caused by differentiation and activation of osteoclasts by making the interaction with the RANKL and interfering the interaction between the RANK and the RANKL, a peptide was manufactured from an amino acid sequence of a loop (e.g., loop 3) of the RANK binding to the RANKL in the structure of the RANK-RANKL complex, and a specific amino acid sequence of the manufactured peptide is shown in Table 2.

TABLE 2

| Category | Amino acid sequence |
|---|---|
| L3-3 | YC WNSDCEC CY RR(SEQ ID NO: 5) |
| L3-3S | YC SNSDCEC CY RR(SEQ ID NO: 4) |
| L3-3N | YC WNSDCEC C RR(SEQ ID NO: 3) |
| L3-3A | SDCECS(SEQ ID NO: 2) |
| L3-3B | SDCECSRR(SEQ ID NO: 1) |

In the loop part (loop 3) of the RANK binding to the RANKL, Cys125 and Cys127 formed a disulfide bond (referred to FIG. 4C), and thus the synthesized peptide was also designed that these two cysteines formed a disulfide bond. However, Cys128 was replaced with Ser to prevent forming of a disulfide bond with neighboring Cys.

Example 6

Examination of Osteoclast Differentiation Inhibitory Effect of Polypeptide

To confirm an osteoclast differentiation inhibitory effect of the polypeptide manufactured in Example 5, the following experiment was performed.

That is, osteoclast precursors of rats were extracted from tibia and the femoral region of 5 to 8-week male rats, and purified. The osteoclast precursors were cultured in α-MEM containing 30 ng/ml of M-CSF and 10% FBS in 96-well plates ($1 \times 10^5$/ml, 200 μl/well). The cells were cultured at 37° C. in a wet atmosphere containing 5% $CO_2$. Differentiation of the osteoclast precursors were measured by a value of tartrate-resistant acid phosphatase (TRAP) activity in vitro. The TRAP staining assay was performed using a matrix Naphthol AS phosphate in 100 mM sodium acetate (pH 5.2). TRAP-positive multinucleated cells were calculated as osteoclast-like multinucleated cells using a microscope, and the assay described above were repeated three times to obtain statistical data.

Figure 6:
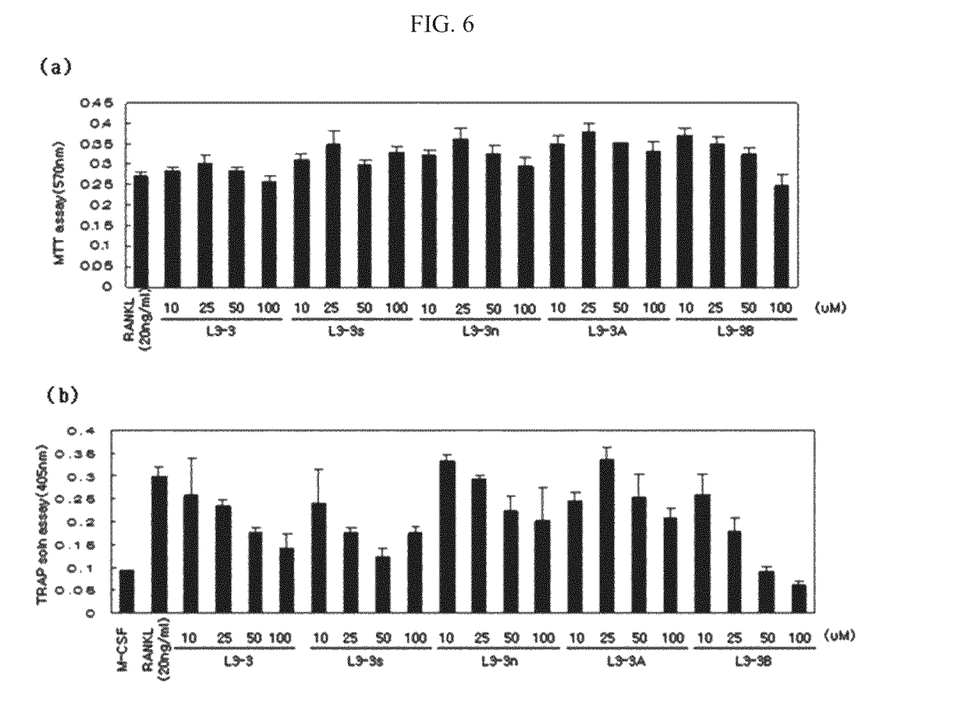
FIG. 6 is a diagram showing cell toxicity and an osteoclast differentiation inhibitory effect of L3-3, L3-3S, L3-3A, L3-3B, and L3-3N according to Example 6 (A is cell toxicity of each peptide confirmed through an MTT assay, and B is a degree of osteoclast differentiation confirmed through a TRAP assay)
Figure 7:
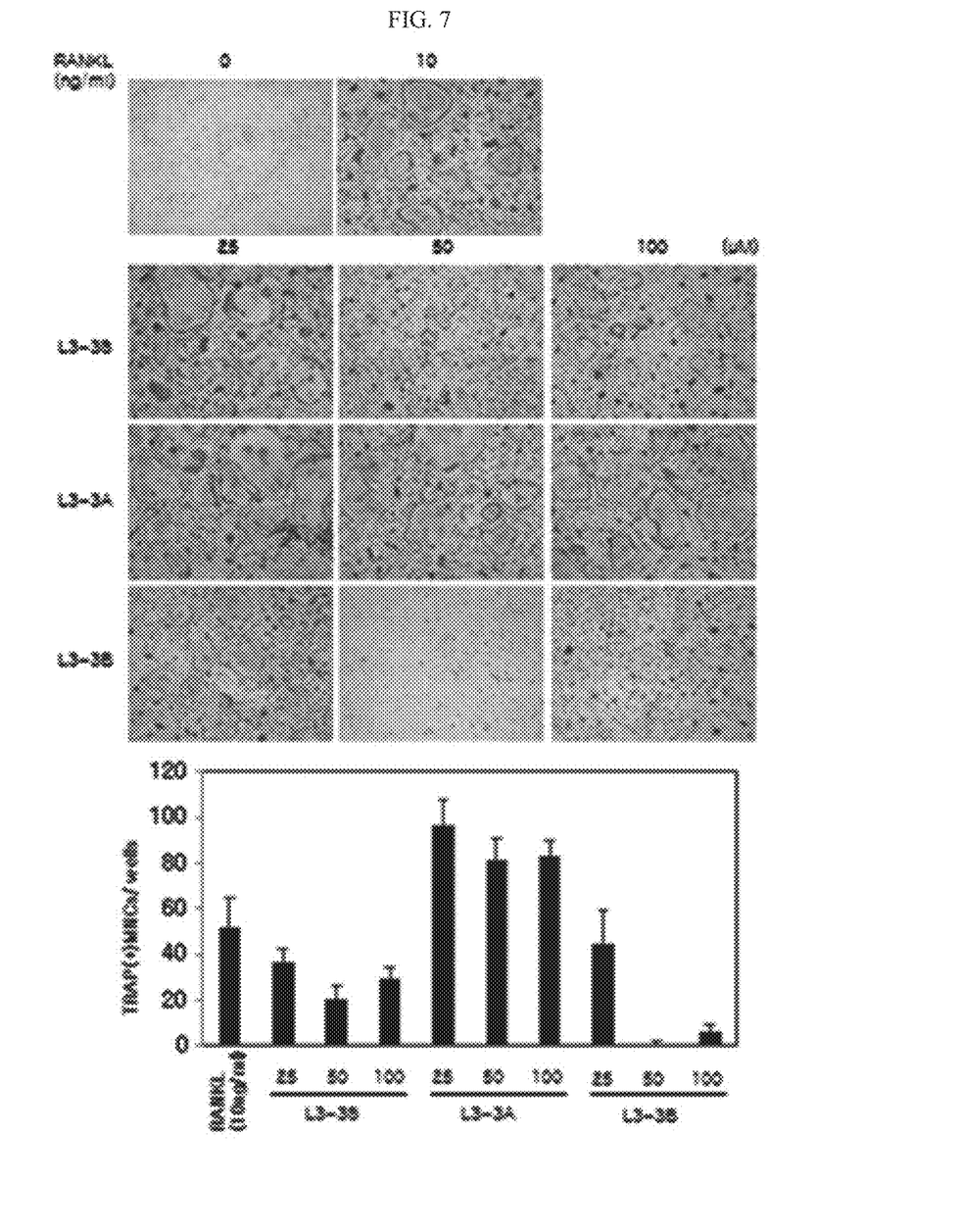
FIG. 7 shows the number of multinucleated cells and the results of the TRAP assay obtained by observing a degree of osteoclast differentiation by an RANKL and a degree of inhibiting differentiation by a peptide to confirm an osteoclast differentiation inhibitory effect of L3-3A, L3-3B, and L3-3S according to Example 6.

In the condition of differentiating osteoclasts by the RANKL, 5 peptides (L3-3, L3-3S, L3-3N, L3-3A, and L3-3B) manufactured in Example 5 were treated by concentrations to observe a degree of inhibition, and the results are shown in FIGS. 6 and 7.

As shown in FIGS. 6 and 7, it was confirmed that all the peptides used in the experiment had no cell toxicity (referred to FIG. 6A), and exhibited a dose-dependent inhibitory effect on osteoclast differentiation (referred to FIG. 6B). Particularly, it was confirmed that L3-3B showed better effects than conventionally disclosed peptides (L3-3 and L3-3S) used as controls. Conventionally (in the prior art), to manufacture a structure similar to the RANK peptide, Cys was tagged at the ends of the L3-3 and L3-3S peptides to make the RANK peptide have a cyclic shape, thereby reducing biobiostability, whereas the peptide according to the present invention was not a cyclic peptide, and thus had excellent biostability and an excellent osteoclast differentiation inhibitory effect. It was confirmed that L3-3B had an extraordinarily higher inhibitory effect than L3-3A, and therefore, it was also shown that Arg-Arg present at C-term played a very important role in activity.

The above description was provided to exemplify the present invention, and it will be understood by those skilled in the related art that various changes in form and details may be made therein without departing from a technical idea or essential characteristics of the present invention. Therefore, it will be understood that Examples described above were exemplary in all aspects, but are not limited to the present invention.

Particularly, in the above-described Examples, experiments were carried out only for the structure of the rat RANKL-RANK complex. Since a sequence was almost the same as those of humans or rats and a sequence of the loop part involved in bonding is exactly the same as those of humans or rats, a structure of the human RANKL-RANK complex can be naturally expected from the structure of the rat RANKL-RANK complex by those skilled in the art, and it is obvious that an osteoclast differentiation inhibitory effect can be obtained by applying the peptide and pharmaceutical composition according to the present invention to a human. In addition, in the above-described Examples, amino acid sequences of new peptides L3-3A and L3-3B and the osteoclast differentiation inhibitory effect of the peptide are confirmed, but a transformed microorganism may be obtained by those skilled in the art by manufacturing a degenerate primer using the amino acid sequence of the peptide according to the present invention, obtaining a gene fragment and a vector including the same by PCR using the previously manufactured primer, and selecting a suitable host cell.

A peptide consisting of an amino acid sequence of SEQ ID NO: 1 according to the present invention is not present in a cyclic shape and has 10 or less amino acids, thereby having better biostability than a conventional peptide to inhibit an RANKL-RANK interaction, being preferable in price during synthesis, and having a better RANKL-RANK interaction inhibitory effect. For this reason, the peptide according to the present invention can be used as an effective component of a composition effectively inhibiting osteoclast differentiation.

In addition, a pharmaceutical composition including the peptide according to the present invention is bound with an RANKL and the peptide according to the present invention, instead of an RANK, thereby inhibiting the interaction between the RANKL and the RANK, and thus inhibiting osteoclast differentiation. As a result, it is expected that the pharmaceutical composition can be applied to prevent or treat bone diseases caused by osteoclast differentiation and activation.

While the invention has been shown and described with reference to certain exemplary embodiments thereof, it will be understood by those skilled in the related art that various changes in form and details may be made therein without departing from the scope of the invention as defined by the appended claims.

What is claimed is:

1. A peptide for inhibiting an interaction between an RANKL and an RANK, comprising 10 or less amino acids, and comprising at least 8 contiguous amino acids having the sequence of SEQ ID NO: 1.

2. The peptide according to claim 1, wherein the peptide has a disulfide bond by linking $3^{rd}$ and $5^{th}$ amino acids.

3. The peptide according to claim 1, wherein the peptide inhibits osteoclast differentiation by inhibiting the interaction between the RANKL and the RANK.

4. A pharmaceutical composition for treating bone diseases, comprising:
   the peptide according to claim 1; and
   a pharmaceutically available carrier.

5. The pharmaceutical composition according to claim 4, wherein the bone disease is a disease induced by differentiation and activation of osteoclasts.

6. The pharmaceutical composition according to claim 5, wherein the bone disease is selected from the group consisting of osteoporosis, osteogenesis imperfecta, hypercalcemia, osteomalacia, rheumatoid arthritis, Paget's disease, bone loss by cancer, and osteonecrosis.

7. The peptide according to claim 1, wherein the peptide is not a cyclic peptide, and a disulfide bond links $3^{rd}$ amino acid and $5^{th}$ amino acid of SEQ ID NO: 1.

8. A peptide comprising at least 8 contiguous amino acids having the sequence of SEQ ID NO: 1, wherein a disulfide bond links $3^{rd}$ amino acid and $5^{th}$ amino acid of the sequence.

9. The peptide according to claim 8, wherein the peptide has 10 or less amino acids and is not a cyclic peptide.

* * * * *

SEQUENCE LISTING

```
<160> NUMBER OF SEQ ID NOS: 5

<210> SEQ ID NO 1
<211> LENGTH: 8
<212> TYPE: PRT
<213> ORGANISM: Artificial Sequence
<220> FEATURE:
<223> OTHER INFORMATION: L3-3B

<400> SEQUENCE: 1

Ser Asp Cys Glu Cys Ser Arg Arg
 1               5

<210> SEQ ID NO 2
<211> LENGTH: 6
<212> TYPE: PRT
<213> ORGANISM: Artificial Sequence
<220> FEATURE:
<223> OTHER INFORMATION: L3-3A

<400> SEQUENCE: 2

Ser Asp Cys Glu Cys Ser
 1               5

<210> SEQ ID NO 3
<211> LENGTH: 12
<212> TYPE: PRT
<213> ORGANISM: Artificial Sequence
<220> FEATURE:
<223> OTHER INFORMATION: L3-3n

<400> SEQUENCE: 3

Tyr Cys Trp Asn Ser Asp Cys Glu Cys Arg Arg
 1               5                  10

<210> SEQ ID NO 4
<211> LENGTH: 13
<212> TYPE: PRT
<213> ORGANISM: Artificial Sequence
<220> FEATURE:
```

```
<223> OTHER INFORMATION: L3-3s

<400> SEQUENCE: 4

Tyr Cys Ser Asn Ser Asp Cys Glu Cys Cys Tyr Arg Arg
 1               5                  10

<210> SEQ ID NO 5
<211> LENGTH: 13
<212> TYPE: PRT
<213> ORGANISM: Artificial Sequence
<220> FEATURE:
<223> OTHER INFORMATION: L3-3

<400> SEQUENCE: 5

Tyr Cys Trp Asn Ser Asp Cys Glu Cys Cys Tyr Arg Arg
 1               5                  10
```